United States Patent [19]

Jorgensen

[11] Patent Number: 4,816,439

[45] Date of Patent: Mar. 28, 1989

[54] THE USE OF HUMAN GROWTH HORMONE FOR THE TREATMENT OF INTOXICATED INDIVIDUALS

[75] Inventor: Karin D. Jorgensen, Vedbaek, Denmark

[73] Assignee: Nordiske Gentofte A/S, Gentofte, Denmark

[21] Appl. No.: 32,053

[22] Filed: Mar. 27, 1987

[51] Int. Cl.$^4$ .............................................. A61K 37/02
[52] U.S. Cl. ..................................... 514/12; 514/810; 514/811
[58] Field of Search .......................... 514/12, 810, 811

[56] References Cited

U.S. PATENT DOCUMENTS 4,452,775  6/1984  Kent ....................................... 424/19
4,657,854  4/1987  Wegfahrt, Jr. ......................... 435/14

OTHER PUBLICATIONS

"Comparison of the Pharmacological Properties of Pituitary and Biosynthetic Human Growth Hormone", pp. 124–131.

*Primary Examiner*—Delbert R. Phillips
*Assistant Examiner*—F. T. Moezie
*Attorney, Agent, or Firm*—Lester Horwitz

[57] ABSTRACT

Human growth hormone is used for the treatment of individuals who are intoxicated with poisonous substances of the type which is degraded in the liver by microsomal enzymes, such as hexobarbiturates or alcohol.

16 Claims, No Drawings

THE USE OF HUMAN GROWTH HORMONE FOR THE TREATMENT OF INTOXICATED INDIVIDUALS

The invention relates to the use of human growth hormone for the treatment of individuals who are intoxicated with poisonous substances of the type which is degraded in the liver by microsomal enzymes.

Furthermore the invention relates to a preparation for treating such intoxicated individuals. Medicine intoxicated patients, such as individuals who have taken overdoses of soporifics, f.ex. barbiturates, have previously been treated with pumping outs and respiration.

So far, however, there has been no actual antidote against toxic substances, f.ex. barbiturates, which are absorbed in the organism and accumulate in the liver where they are slowly degraded enzymatically.

The present invention is based on the observation that the presence of hGH reduces the time in which toxic substances of the type indicated are active. It is thus assumed that the the breaking down of toxic substances, f.ex. barbiturates, in the liver may be accelerated through the administration of human growth hormone, hGH. The reason for this effect is not known, but it is assumed that hGH either activates the degradable enzymes or causes increased production of such enzymes.

In accordance herewith the effect of hGH is one which functions in connection with all toxic substances of the type which is mainly absorbed and broken down in the liver.

Apart from barbiturates such toxic substances comprise alcohol. In consequence hGH is suitable for treating alcoholic poisoning.

Any in itself known preparation containing a pharmacologically active dose of hGH may be used for treating intoxicated individuals. The method of administration is not important to the effect achieved, if only it is ensured that the quantity of hGH preparation administered has a certain magnitude, normally corresponding to a maximum of 100 IU/kg body weight.

The hGH preparation applied may appropriately be administered in injectable doses of 0.1–10 IU/kg body weight, administered at intervals up to 10 times.

Instead the hGH preparation may be administered in the form of an infusion preparation where the hGH preparation is continuously being administered to the patient in amounts of appropriately up to 100 IU/kg body weight. This amount should be administered over not more than 1 day, but in certain instances, and if required, the treatment may be continued over a longer period of time.

One method of administration is the use of nasal preparations, f.ex. in spray form, where the hGH preparation contains substances which facilitate the penetration of mucous membranes.

Depending on the method of administration the preparation may contain any suitable vehicles or subsidiary materials of the usual kinds and which may be selected by a person skilled in the art.

In the following the invention will be illustrated by means of some working examples.

EXAMPLE 1

Biosynthetic human growth hormone, pituitary human growth hormone (Nanormon ®) and pituitary 22K, all manufactured by Nordisk Gentofte A/S, were tested for their effect on the duration of hexobarbital narcosis in mice. The three growth hormone preparations were administered subcutaneously to mice in dosages of 0.25, 2.5 and 25 IU/kg body weight. Nanormon ® buffer was used as placebo.

The freeze-dried materials were dissolved in 3 ml distilled water to obtain isotonic solutions. Further dilutions were made with Nanormon ® buffer. The stock solutions contained 1.4 mg protein/ml (B-hGH), 1.1–1.5 mg/ml (P22K) and 1.6 mg/ml protein (Nanormon ®), and the biological potencies as determined by a preliminary tibia test were 2.0 IU/mg, 1.9 IU/mg and 2.6 IU/mg, respectively.

25 IU/kg, 2.5 IU/kg and 0.25 IU/kg body weight was administered in volumes of 0.2 ml/mouse, i.e. 10 ml/kg body weight subcutaneously in the neck. The same volumes of Nanormon ® buffer was used as placebo.

A 0.4% solution of hexobarbital in distilled water added approximately 10 µl 5N NaOH per ml was prepared. NaOH was from the Chemical Control Department. The mice were dosed with 0.5 ml (100 mg/kg) intraperitoneally.

Male and female NMRI mice from Gl. Bomholtgaard, Ry, were acclimatized for 4–7 days before use at $20\pm1°$ C., $60\pm5\%$ relative humidity, air change 16 per hour and light from 7.30 a.m. till 7.30 p.m. The animals had free access to Altromin diet and drinking water and were kept in rectangular polypropylene or Macrolon ® cages with Spanvall beech bedding. When the mice were used, they were $20\pm2$ g and 26–31 days old (male mice), 28–33 days old (female mice).

Each dosage of growth hormone was administered to four groups of 10 mice, the two groups having growth hormone s.c. ½ hour before hexobarbital i.p. and the other two groups having growth hormones 2 hours before hexobarbital dosing. The treatments were randomly assigned to the groups and a placebo group was included each experimental day. During the narcosis the mice were placed on a heated operation table (37° C.) (from Hugo Sachs Elektronik), and the time from disappearance till reappearance of the righting reflex was registered as the sleeping time.

Results

In table 1A and 12 the results are known for male and female mice respectively, when the growth hormone preparations were administered ½ h before hexobarbital dosing. All three growth hormone preparations caused a significant shortening of the hexobarbital sleeping time (for significance levels see the tables). Effects were observed even after 0.25 iu/kg—nearly therapeutic doses. There were no differences between male and female mice. In all groups the onset of narcosis was within a few minutes after hexobarbital i.p., and it was not changed by the previous dosing of growth hormones. Tables 2A and 2B show the corresponding results for male and female mice when the growth hormones were dosed 2 h prior to hexobarbital. Apparently the effects of growth hormone are practically absent. This means that the effect is of rather short duration. The mechanism of action is not known, and the effect has not been reported in the literature. As the other pharmacological results do not support in any way a central stimulating action of growth hormone, other explanations may be that growth hormone promotes redistribution of hexobarbital from the brain to other tissues or perhaps causes an induction of the microsomal enzymes in the liver responsible for the oxidative metabolism of barbiturates.

Conclusion

Biosynthetic human growth hormone, Nanormon® and pituitary 22K human growth hormone, all decrease the duration of hexobarbital narcosis in mice significantly. Effects are seen even after 0.25 Iu/kg body weight (approximately human therapeutic doses). The effect is of rather short duration, less than 2–2½ hours.

Duration of hexobarbital narcosis in mice.

The doses of growth hormone were injected subcutaneously 30 minutes before intraperitoneal administration of hexobarbital, 100 mg/kg.

| Treatment | Doses IU/kg b. wt. s.c. | N Mice Sex | Loss of righting reflex, min. after hexobarbital $\overline{X} \pm$ S.E.M. | Reappearance of righting reflex, min after hexobarbital $\overline{X} \pm$ S.E.M. | Duration of narcosis (min.) $\overline{X} \pm$ S.E.M. | Ratio of duration |
|---|---|---|---|---|---|---|
| Placebo | — | 20 female | 3.8 ± 0.2 | 43 ± 3 | 39 ± 3.4 | 1.000 |
| Nanormon ® | 25 | 10 female | 4.5 ± 0.5 | 30 ± 5 | 25 ± 4.5[1] | 0.641 |
|  | 2.5 | 10 female | 4.1 ± 0.4 | 29 ± 3 | 26 ± 2.8[1] | 0.667 |
|  | 0.25 | 10 female | 4.3 ± 0.3 | 35 ± 3 | 31 ± 2.9 | 0.795 |
| Biosynthetic human growth hormone | 25 | 10 female | 4.8 ± 0.3 | 25 ± 3 | 20 ± 2.5[2] | 0.513 |
|  | 2.5 | 10 female | 3.7 ± 0.3 | 32 ± 3 | 28 ± 3.5 | 0.718 |
|  | 0.25 | 10 female | 4.1 ± 0.3 | 34 ± 3 | 30 ± 3.3 | 0.769 |
| Pituitary 22K | 25 | 10 female | 5.3 ± 0.6 | 32 ± 4 | 27 ± 3.8[1] | 0.692 |
|  | 2.5 | 10 female | 3.9 ± 0.4 | 18 ± 1 | 15 ± 1.3[3] | 0.385 |
|  | 0.25 | 10 female | 3.5 ± 0.1 | 34 ± 3 | 31 ± 2.7 | 0.795 |

[1] $p < 0.05$.
[2] $p < 0.01$.
[3] $p < 0.001$ (Student's t-test)

Duration of hexobarbital narcosis in mice.

The doses of growth hormone were injected subcutaneously 120 minutes before intraperitoneal administration of hexobarbital, 100 mg/kg.

| Treatment | Doses IU/kg b. wt. s.c. | N Mice Sex | Loss of righting reflex, min. after hexobarbital $\overline{X} \pm$ S.E.M. | Reappearance of righting reflex, min after hexobarbital $\overline{X} \pm$ S.E.M. | Duration of narcosis (min.) $\overline{X} \pm$ S.E.M. | Ratio of duration |
|---|---|---|---|---|---|---|
| Placebo | — | 30 male | 3.3 ± 0.2 | 35 ± 2 | 32 ± 2.5 | 1.000 |
| Nanormon ® | 25 | 10 male | 3.0 ± 0.3 | 44 ± 5 | 41 ± 5.2 | 1.281 |
|  | 2.5 | 10 male | 2.9 ± 0.4 | 42 ± 4 | 39 ± 3.8 | 1.219 |
|  | 0.25 | 10 male | 4.0 ± 0.2 | 23 ± 1 | 20 ± 1.5[1] | 0.625 |
| Biosynthetic human growth hormone | 25 | 10 male | 3.4 ± 0.3 | 45 ± 3 | 43 ± 4.0 | 1.344 |
|  | 2.5 | 10 male | 3.1 ± 0.3 | 29 ± 4 | 27 ± 4.5 | 0.844 |
|  | 0.25 | 10 male | 3.7 ± 0.1 | 34 ± 4 | 31 ± 3.6 | 0.969 |
| Pituitary 22K | 25 | 10 male | 2.9 ± 0.2 | 33 ± 5 | 30 ± 4.9 | 0.938 |
|  | 2.5 | 10 male | 2.8 ± 0.5 | 44 ± 7 | 41 ± 7.1 | 1.281 |
|  | 0.25 | 10 male | 4.0 ± 0.2 | 27 ± 2 | 23 ± 1.7 | 0.719 |

[1] $p < 0.05$ (Student's t-test)

The doses of growth hormone were injected subcutaneously 30 minutes before intraperitoneal administration of hexobarbital, 100 mg/kg.

| Treatment | Doses IU/kg b. wt. s.c. | N Mice Sex | Loss of righting reflex, min. after hexobarbital $\overline{X} \pm$ S.E.M. | Reappearance of righting reflex, min after hexobarbital $\overline{X} \pm$ S.E.M. | Duration of narcosis (min.) $\overline{X} \pm$ S.E.M. | Ratio of duration |
|---|---|---|---|---|---|---|
| Placebo | — | 20 male | 3.4 ± 0.2 | 40 ± 3 | 37 ± 2.6 | 1.000 |
| Nanormon ® | 25 | 10 male | 4.0 ± 0.3 | 38 ± 2 | 34 ± 2.2 | 0.919 |
|  | 2.5 | 10 male | 4.0 ± 0.3 | 25 ± 2 | 21 ± 2.1[3] | 0.568 |
|  | 0.25 | 10 male | 3.3 ± 0.3 | 25 ± 3 | 22 ± 2.7[2] | 0.595 |
| Biosynthetic human growth hormone | 25 | 10 male | 4.4 ± 0.3 | 28 ± 2 | 24 ± 2.6[2] | 0.649 |
|  | 2.5 | 10 male | 4.5 ± 0.8 | 30 ± 4 | 26 ± 4.5[1] | 0.703 |
|  | 0.25 | 10 male | 3.4 ± 0.3 | 31 ± 2 | 28 ± 2.5 | 0.757 |
| Pituitary 22K | 25 | 10 male | 5.3 ± 1.0 | 22 ± 3 | 17 ± 2.5[3] | 0.459 |
|  | 2.5 | 10 male | 4.7 ± 0.3 | 30 ± 5 | 25 ± 4.9[1] | 0.676 |
|  | 0.25 | 10 male | 3.9 ± 0.2 | 29 ± 3 | 26 ± 3.2[1] | 0.703 |

[1] $p < 0.05$.
[2] $p < 0.01$.
[3] $p < 0.001$ (Student's t-test)

Duration of hexobarbital narcosis in mice.

The doses of growth hormone were injected subcutaneously 120 minutes before intraperitoneal administration of hexabarbital, 100 mg/kg.

| Treatment | Doses IU/kg b. wt. s.c. | N Mice Sex | Loss of righting reflex, min. after hexobarbital $\overline{X} \pm$ S.E.M. | Reappearance of righting reflex, min after hexobarbital $\overline{X} \pm$ S.E.M. | Duration of narcosis (min.) $\overline{X} \pm$ S.E.M. | Ratio of duration |
|---|---|---|---|---|---|---|
| Placebo | — | 30 female | 3.7 ± 0.2 | 39 ± 4 | 35 ± 4.0 | 1.000 |

-continued

| Treatment | Doses IU/kg b. wt. s.c. | N Mice Sex | Loss of righting reflex, min. after hexobarbital $\bar{X} \pm$ S.E.M. | Reappearance of righting reflex, min after hexobarbital $\bar{X} \pm$ S.E.M. | Duration of narcosis (min.) $\bar{X} \pm$ S.E.M. | Ratio of duration |
|---|---|---|---|---|---|---|
| Nanormon ® | 25 | 10 female | 3.5 ± 0.3 | 42 ± 5 | 38 ± 4.8 | 1.086 |
| | 2.5 | 10 female | 3.3 ± 0.2 | 37 ± 6 | 34 ± 6.1 | 0.971 |
| | 0.25 | 10 female | 3.5 ± 0.2 | 33 ± 6 | 30 ± 5.6 | 0.857 |
| Biosynthetic | 25 | 10 female | 3.5 ± 0.2 | 38 ± 3 | 35 ± 3.5 | 1.000 |
| human growth | 2.5 | 10 female | 2.8 ± 0.3 | 35 ± 3 | 32 ± 2.6 | 0.914 |
| hormone | 0.25 | 10 female | 3.6 ± 0.3 | 35 ± 4 | 32 ± 4.3 | 0.914 |
| Pituitary 22K | 25 | 10 female | 3.9 ± 0.3 | 37 ± 5 | 33 ± 4.6 | 0.943 |
| | 2.5 | 10 female | 3.3 ± 0.4 | 33 ± 3 | 30 ± 3.5 | 0.857 |
| | 0.25 | 10 female | 4.1 ± 0.3 | 17 ± 1 | 13 ± 1.6[(2)] | 0.371 |

[(2)] $p < 0.01$ (Student's t-test)

EXAMPLE 2

Experiments were carried out as mentioned in example 1, substituting pentabarbital for hexobarbital.

A similar effect was found, except that it was more pronounced on female mice than on male mice.

We claim:

1. A method for treating individuals acutely intoxicated with poisonous substances that are degraded in the liver by microsomal enzymes comprising administering an effective amount of human growth hormone to said individuals.

2. The method as in claim 1, wherein the poisonous substance is a barbiturate.

3. The method as in claim 2, wherein the poisonous substance is hexobarbital.

4. The method as in claim 1, wherein the poisonous substance is alcohol.

5. The method as in claim 1 wherein the effective amount comprises doses of 0.1–10 Iu/kg body weight given at intervals of up to 10 times.

6. The method as in claim 1, wherein human growth hormone is administered via infusion.

7. The method, as in claim 1 wherein said human growth hormone is administered in a composition comprising human growth hormone and a pharmaceutically acceptable carrier.

8. The method, as in claim 6 wherein the effective amount comprises up to 100 Iu/kg body weight administered over a period of time of up to 1 day.

9. The method, as in claim 6 wherein the effective mount comprises up to 100 Iu/kg administered for more than 1 day.

10. A method for accelerating the breakdown of toxic substances which accumulate in the liver comprising administering to an acutely intoxicated patient, in need of such treatment an effective amount of human growth hormone.

11. The method, as in claim 10 wherein the toxic substance is a barbituate.

12. The method, as in claim 10 wherein the toxic substance is hexobarbital.

13. The method, as in claim 10 wherein the toxic substance is alcohol.

14. The method, as in claim 10 wherein the effective amount comprises doses of 0.1–10 Iu/kg body weight given at intervals of up to 10 times.

15. The method, as in claim 10 wherein the human growth hormone is administered as a composition comprising human growth hormone and a pharmaceutically acceptable carrier.

16. The method, as in claim 15 wherein the composition is administered by infusion.

* * * * *